United States Patent [19]

Brennan et al.

[11] Patent Number: 5,162,223
[45] Date of Patent: Nov. 10, 1992

[54] **HYBRIDOMAS AND RESULTING MONOCLONAL ANTIBODIES DIRECTED AGAINST ANTIGENS OF *BORDETELLA PERTUSSIS***

[75] Inventors: Michael J. Brennan, Kensington; Charles R. Manclark, Rockville; Zhong Ming Li, Bethesda, all of Md.

[73] Assignee: The United States of America as represented by the Secretary of the Department of Health and Human Resources, Washington, D.C.

[21] Appl. No.: 312,097

[22] Filed: Feb. 17, 1989

[51] Int. Cl.$^5$ .................. C12N 15/00; C12N 5/00; H01R 31/08; A61K 39/00
[52] U.S. Cl. .................. 435/240.26; 935/103; 935/106; 436/513; 530/388.1; 530/388.2; 530/388.4; 425/240.27
[58] Field of Search .................. 530/387, 388.1, 388.2, 530/388.4; 435/240.27; 436/513; 935/103, 106

[56] References Cited

PUBLICATIONS

Abstracts and Program of the Sixth International Symposium on Pertussis, Mandark, Charles R. 1990, (ed) Dept. of Health & Human Services, Pub. No. (FDA) 90-1162, pp. 145-146, Leininger et al.
Pollack et al., "Specificity and Cross-Reactivity of Monoclonal Antibodies Reactive with the Core and Lipid A Regions of Bacterial Lipopolysaccharide," Journal of Infectious Diseases, vol. 159, No. 2, Feb. 1989, pp. 168-188.
Brennan et al., Inf & Immun. 56(12):3189. 1988.
Li et al., Inf & Immun. 56(3):699. 1988.
Li et al., Inf & Immun. 56(12):3184. 1988.
Gustafson et al., J. Clin. Microbiol. 26(19):2077. 1988.
Girard et al., Immunology 56:481. 1985.

*Primary Examiner*—Elizabeth C. Weimar
*Assistant Examiner*—Suzanne Ziska
*Attorney, Agent, or Firm*—Cushman, Darby & Cushman

[57] ABSTRACT

A panel of monoclonal antibody (Mab) producing hybridomas directed against various antigens of *Bordetella pertussis* are disclosed herein. The hybridomas and the antigens that the resulting monoclonals are directed against include: (1) BPG10F8C3 and BPE8D8-B1—lipooligosaccharide A (LOS A), serotype 1; (2) BPD5, BPE6, and BPF2—fimbriae, serotype 2; (3) BPE3, BPE8 and BPD8—69 kDa nonfimbrial protein, serotype 3; and (4) BPB7, BPC10, BPD4, BPD6, BPD9, and BPF5—fimbriae, serotype 6.

18 Claims, No Drawings

HYBRIDOMAS AND RESULTING MONOCLONAL ANTIBODIES DIRECTED AGAINST ANTIGENS OF *BORDETELLA PERTUSSIS*

FIELD OF INVENTION

The present invention relates to hybridomas and monoclonal antibodies produced therewith which are reactive with certain antigens of *Bordetella pertussis*.

BACKGROUND OF INVENTION

*Bordetella pertussis* is the bacterial pathogen responsible for whooping cough in humans. Presently, the only widely-available commercial diagnostic probe available to detect *B. pertussis* in naso-pharyngeal aspirates or in cultures from patients with clinical symptoms of pertussis is a crude polyclonal antiserum that typically gives high background in routine immunofluorescence assays.

In addition to its diagnostic applications, polyclonal antiserum to *B. pertussis* has also been employed to establish serotypes for *B. pertussis*. Serotype markers for the bacterium have been defined by the ability of strain-specific polyclonal antisera to agglutinate the bacteria.

E. K. Andersen first identified five distinctive agglutinogen factors in 1953 (Acta Pathol. Microbiol. Scand. 33:202–224 (1953)), and Eldering et al. subsequently added agglutinogen factor 6 (J. Bacteriol. 74:133–136 (1957)). In fact, it is the use of mono-specific polyclonal antisera (Preston factors 1–3) in combination with U.S. Reference Factor 1-6 antisera which has permitted *B. pertussis* to be distinguished from the closely related species *B. bronchiseptica* and *B. parapertussis.*

Following whooping cough outbreaks, it has been noted that there tends to be a prevalence of certain *B. pertussis* serotypes, and the serum agglutinin titers of human vaccinees appear to correlate with clinical protection from pertussis. Thus, identification of specific agglutinogens to *B. pertussis* is of potential importance since they may serve as protective antigens.

Some of the agglutinogen factors have been defined, for instance, the expression of lipooligosacccharide A (LOS A) by *B. pertussis* cells appears to correlate with the presence of the serotype 1 agglutinogen factor. Likewise, fimbrial agglutinogens have been found to correspond to serotype 2-, 3-and 6-containing cells, and a nonfimbrial 69 kDa outer membrane protein appears to correlate to serotype 3 cells.

In view of the above, the present inventors sought to create *Bordetella pertussis* hybridomas and serotype-specific monoclonal antibodies (Mabs) therefrom in order to specifically detect *B. pertussis* organisms and the antigens that they produce, and to advantageously utilize such Mabs for diagnostic, manufacturing and research purposes.

SUMMARY OF INVENTION

A panel of monoclonal antibody (Mab) producing hybridomas directed against various outer membrane antigens of *Bordetella pertussis* are disclosed herein. The hybridomas and the antigens that the resulting monoclonals are directed against include: (1) BPG10F8C3 and BPE8D8B1—lipooligosaccharide A (LOS A), serotype 1; (2) BPD5, BPE6, and BPF2—fimbriae, serotype 2; (3) BPE3, BPE8 and BPD8—69 kDa nonfimbrial protein, serotype 3; and (4) BPB7, BPC10, BPD4, BPD6, BPD9, and BPF5—fimbriae, serotype 6. Hybridomas and Mabs directed to serotypes 4 and 5 have not as yet been defined.

The hybridomas of the present invention are advantageous over hybridomas of the prior art in that they have been selected for their ability to grow well in culture and to effectively produce ascites.

Likewise, the monoclonal antibodies of the present invention also possess advantageous features, namely: (a) they are superior to crude polyclonal antiserum in diagnostic immunofluorescence assays and in that they are highly specific for *B. pertussis* organisms and they produce results which correlate with culture positive patients; (b) they show no cross-reactivity with other bacteria except the closely related species *B. bronchiseptica* and *B. parapertussis;* (c) they are useful for serotyping *B. pertussis* strains and for determining whether particular antigens are being expressed; (d) several have shown very high titers in bacterial agglutination assays and in ELISA and have been employed in immunoblotting procedures at dilutions of 1:1000 or greater, thus, they may be useful in regulating acellular pertussis vaccines; (e) they have been successfully employed in immunoelectronmicroscopy to determine serotype-specificity; and (f) they have been successfully linked to agarose for use in affinity purification procedures, thus, they may be commercially beneficial in the manufacture of purified reagents or vaccine components.

BRIEF DESCRIPTION OF THE TABLES

Table 1. Agglutination of bacterial strains by monoclonal antibodies reactive with *B. pertussis* LOS A, serotype 1.

Table 2. Agglutination of serotype-specific *B. pertussis* strains by monoclonal antibodies to serotype 3 (69 kDa protein) or serotype 2 or 6 fimbriae and polyclonal antiserum to the 69 kDa protein.

Table 3. Agglutination of *B. pertussis* cells by serotype 2- and serotype 6- reactive monoclonal antibodies.

DETAILED DESCRIPTION OF INVENTION

All references cited below are to be specifically incorporated herein by reference.

A. MICROORGANISMS

Strains of *B. bronchiseptica* were provided by David Bemis, University of Tennessee, Knoxville, TN. *B. pertussis* strains Tohama I, 134, 10901 and 11615 were provided by Mark S. Peppler, University of Alberta, Edmonton, Alberta, Canada. The Tn5 insertion mutants BP325, BP326, BP338, BP353 and BP354 were provided by D. Alsion Weiss, Medical College of Virginia, Richmond, VA. The remaining *B. pertussis* strains (e.g. 114, and 432) are available through the Laboratory of Pertussis, CBER, FDA, NIH, Bethesda, MD.

Some serotyping antisera were provided by N.W. Preston, University of Manchester, U.K.

*Bordetella pertussis* cells were cultured on Bordet-Gengou agar medium (Difco Laboratories, Detroit, MI) containing 15% sheep blood and subcultured and grown in liquid Cohen-Wheeler or modified Stainer-Scholte medium (strains 114 and 432) as described by Cowell et al. (Infect. Immun. 55:916–922 (1987)) (see also, Li et al. Infection and Immunity 56(3);699–702 (1988)).

Protein was purified from the bacteria as described below, or the cells were fixed in 0.2% formaldehyde and serotyped by the microagglutination assay of Manclark et al. (*Manual of Clinical Laboratory Immunology,*

Rose, Friedman and Fahey, eds., pp. 388–394, Am. Soc. for Micro, Wash. D.C. (1986)) with U.S. Reference Factor 1 to 6 antisera (Eldering agglutinogen 1 to 6 polyclonal antisera) (Eldering et al , J. Bacteriol. 74:133–136 (1957)).

For adsorption studies, 0.5 ml of a 1:10 dilution of U.S. Reference Factor 3 Antiserum was incubated with $10^{11}$ formaldehyde-fixed BP353 cells overnight at 25° C. Bacteria were removed by centrifugation and the resulting antiserum was used for agglutination studies.

B. PROTEIN PURIFICATION

1. 69 kDa Protein

Crude outer membrane protein preparations containing the 69 kDa *B. pertussis* protein were obtained by heating $6 \times 10^{12}$ washed bacteria, resuspended in 30 ml of phosphate buffered saline (PBS: 0.01M PO$_4$, 0.15M NaCl, pH 7.2) for one hour at 60° C. The 69 kDa protein was purified therefrom by affinity chromatography using the monoclonal antibody BPE3 linked to agarose as described by Brennan et al. (Infection and Immunity, 56(12):3189–3195 (1988)).

The resulting purified protein was used to produce polyclonal antisera by immunizing five mice subcutaneously with 20 µg of protein per mouse in Freund complete adjuvant, followed in 4 weeks by a secondary injection with incomplete adjuvant. The mice were bled 7 days after the second injection, the sera were pooled, and agglutination tests were performed after nonspecific agglutination was reduced by adsorption of the sera with 25% kaolin by the method of Zhang et al. (Infect. Immun. 48:422–427 (1985)). Mouse sera obtained prior to immunization were negative in the agglutination assays.

2. Fimbriae Protein

Serotype 2 and serotype 6 fimbriae were isolated from *B. pertussis* strain 325 and 114 cells, respectively, by mechanical shearing using a Sorvall Omni-mixer followed by ammonium sulfate precipitation as described by Cowell et al., supra (see also, Li et al., Infection and Immunity 56(12):3184–3188 (1988)). These crude fimbrial preparations were used in the production of hybridomas and in indirect enzyme-linked immunosorbent assays (ELISA).

C Monoclonals

Hybridomas were established by standard procedures (e.g., Fazekas de St. Groth and Scheidegger, J Immunol. Meth. 35:1–21 (1980)). More specifically, hybridomas BPG10F8C3 and BPE8D8B1 were prepared by immunizing BALB/c mice with partially purified preparations of fimbriae from *B. pertussis* strain strain 325 (serotype 1.2.3.4) or 114 (serotype 1.3.6), and the spleen cells fused with the plasmacytoma cell line SP2/0.

Likewise, BPE3, BPD8 and BPE8 were obtained by fusion of spleen cells from BALB/c mice, immunized with *B. pertussis* strain BP353 (serotype 1.3), to the plasmacytoma cell line SP 2/0.

Similarly, hybridomas BPF2, BPD5, BPE6, BPB7, BPD4, BPD6, BPD9, BPF5 and BPC10 were made by subcutaneously immunizing BALB/c mice with crude fimbrial preparations isolated from *B. pertussis* strain 325 (serotype 1.2.3.4) or 114 (serotype 1.3.6) and the spleen cells fused with the SP2/0 cell line.

The protocol employed above comprised injecting mice with protein or with $5 \times 10^8$ a formaldehyde-fixed bacteria intraperitoneally (or subcutaneously when so noted) three times at 2-week intervals, and an intravenous injection was given 3 days before fusion.

Hybridoma supernatants were initially screened for the presence of monoclonal antibodies by bacterial agglutination (Manclark et al., supra) and by indirect enzyme-linked immunosorbent assays (ELISA) using microtiter plates coated with fixed *B. pertussis* cells.

Immunoglobulin isotypes were determined by enzyme-linked immunosorbent assays with specific anti-mouse immunoglobulin reagents (Southern Biotechnology Assoc., Inc., Birmingham, Ala.). Monoclonal antibodies were then purified from ascitic fluid by precipitation with 50% ammonium sulfate followed by chromatography on DEAE-cellulose with a 0 to 0.2M potassium chloride gradient for the elution of antibodies of the immunoglobulin G isotype, or by gel filtration with Sepharose 4B for antibodies of the immunoglobulin M isotype.

The purity of the resulting immunoglobulin fractions was assessed by sodium dodecyl sulfate-polyacrylamide gel electrophoresis (SDS-PAGE).

D. Agglutination Tests

Supernatants from the hybridomas described above were assessed to determine their ability to agglutinate various *B. pertussis* strains. The results of these agglutination tests are provided below in Table 1—BPG10F8C3 and BPE8D8B1 (anti-LOS A); Table 2—BPE3, BPE8 and BPD8 (anti-69 kDa protein), as well as BPF2 and BPC10 (anti-fimbriae); and Table 3—BPD5, BPE6, BPF2, BPB7, BPC10, BPD4, BPD6, BPD9, and BPF5 (anti-fimbriae).

As depicted in Table 1, hybridomas BPG10F8C3 and BPE8D8B1 produced monoclonal antibodies which agglutinated *B. pertussis* strains of various serotypes although strains Tohama I and Tohama III were most strongly agglutinated. Four strains of *B. bronchiseptica* and three strains of *B. parapertussis* were not agglutinated, nor were other gram-negative bacteria such as *Escherichia coli, Haemophilus influenzae, Neisseria gonorrhoeae, Neisseria meningitidis,* and *Salmonella typhimurium.*

BPG10F8C3 and BPE8D8B1 both produced monoclonal antibodies of the immunoglobulin G$_3$ subclass (IgG$_3$).

Table 2 shows that the three hybridomas—BPE3, BPE8, and BPD8 produce monoclonal antibodies that strongly agglutinate the immunizing BP353 cells and an additional serotype 1.3 strain, BP354. These monoclonal antibodies also agglutinate some (but not all) *B. pertussis* cells of serotypes 1 3.6, 1.2.3.4, and 1.2.3.4.6. In all cases, the agglutination titer was highest with BPE3. These antibodies did not agglutinate serotype 1 or nontypable strains of *B. pertussis,* four strains of *B. bronchiseptica,* three strains of *B. parapertussis,* and other gram-negative bacteria, including *Escherichia coli, Haemophilus influenzae, Neisseria gonorrhoeae, Neisseria meningitidis,* and *Salmonella typhimurium.*

BPE3 produced monoclonal antibodies of the immunoglobulin M subclass (IgM), while BPE8 and BPD8 produced monoclonal antibodies of the immunoglobulin G$_1$ subclass (IgG$_1$)

Table 3 shows that monoclonal antibodies from hybridomas produced by immunizing mice with type 2 (BPF2, BPE6 and BPD5) fimbriae agglutinated *G. pertussis* serotype 1.2.3.4 and 1.2.3.4.6 *B. pertussis* cells but not serotype 1.3.6 strains. Monoclonal antibodies from hybridomas produced by immunizing mice with type 6 (BPC10, BPB7, BPD4, BPD6, BPD9 and BPF5) fimbriae agglutinated serotype 1.2.3.4.6 and 1.3.6 strains but not serotype 1.2.3.4 strains. None of these antibodies agglutinated serotype 1.3, 1 or nontypable strains of *B. pertussis*.

The hybridomas which produced monoclonal antibodies reactive with type 2 fimbriae, namely BPF2, BPD5 and BPE6 were of the immunoglobulin subclasses $IgG_1$, $IgG_{2a}$, and $IgG_{2b}$, respectively. Monoclonal antibodies which were reactive with the type 6 fimbriae, i.e., antibodies from hybridomas BPC10, BPB7, BPD4, BPD6, BPD9 and BPF5 were found to be of the immunoglobulin subclasses $IgG_1$, $IgG_{2b}$, $IgG_{2a}$, $IgG_{2a}$ $IgG_{2a}$, and $IgG_{2b}$, respectively.

E. SDS-PAGE and Western Blot Analysis

Whole-cell lysates, crude bacterial extracts and purified proteins were analyzed by sulfate-polyacrylamide gel electrophoresis (SDS-PAGE) on a 10% resolving gel with a 3% stacking gel (Laemmli, Nature (London) 227:680–685 (1970)). Samples were solubilized in electrophoresis buffer containing 0.1% SDS and 0.1M dithiothreitol and boiled for 5 minutes except for fimbriae which were boiled for only 1 minute prior to application on the gel.

Application of the fimbriae to the gel resulted in the appearance of multiple oligomeric fimbrial units larger than the monomeric subunit as visualized by Coomassie blue or silver staining.

For Western blot (immunoblot) analysis, proteins were electroblotted from the gel onto nitrocellulose paper (BA-85; Schleicher & Schuell, Inc., Keene, NH) for 1 hour at 100 V in 0.025M Tris-0.192M glycine (pH 8.3) buffer containing 20% methanol as described by Towbin et al. (Proc. Natl. Acad. Sci. USA 76:4350–4354 (1979)).

Nitrocellulose filters were blocked in Tris-buffered saline (0.02M Tris-0.5M NaCl, pH 7.5) containing 0.5% bovine serum albumin (BSA) with shaking overnight at 25° C. The filters were then incubated with hybridoma supernatants concentrated 10-fold with 50% ammonium sulfate diluted 1:100, or with ascitic fluid diluted 1:1000 in Tris-buffered saline containing 0.05% Tween 20 and 0.2% sodium azide for 2 hours at 25° C.

After extensive washing, the filters were incubated for an additional 2 hours in a 1:1,000 dilution of alkaline phosphatase-conjugated goat anti-mouse immunoglobulin (Sigma Chemical Co., St. Louis, MO), or with peroxidase-conjugated goat anti-mouse immunoglobulin (Bio-Rad, Richmond, CA).

The filters were developed with the Protoblot substrate system (Promega Biotec, Madison, WI) to detect alkaline phosphatase-conjugated antibodies, or with 4-chloro-1-naphthol as the peroxidase substrate. A similar procedure was used to detect bands reactive with U.S. Reference Factor 3 antiserum with this rabbit polyclonal antiserum diluted 1:300, followed by a 1:1000 dilution of peroxidase-conjugated goat anti-rabbit immunoglobulin (Bio-Rad, Richmond, CA).

1. G10F8C3 and E8D8B1

Monoclonal antibodies G10F8C3 and E8D8B1 detected a single diffuse band migrating near the gel front on lanes containing lysates of agglutination-positive *B. pertussis* strains. The immunoreactive band was confirmed to be LOS A by Western blot analysis of Tohama I LOS.

Agglutinogen 1 was common to all *B. pertussis* strains agglutinated by monoclonals G10F8C3 and E8D8B1. The U.S Reference Agglutinogen Factor 1 Antiserum (Eldering agglutinogen 1 polyclonal antiserum) reacted strongly with LOS A on immunoblots of Bordetella cell lysates, as did monoclonal antibody G10F8C3. However, LOS A and agglutinogen factor 1 are not identical since agglutinogen factor 1 antiserum agglutinated *B. pertussis* 134, which did not express LOS A and was not agglutinated by the monoclonal antibodies.

No cross-reactivity of the anti-LOS A monoclonal antibodies was observed with LOSs of other bacterial genera, however, these monoclonal antibodies did react with LOS AB strains of *B. bronchiseptica*.

2. BPE3, BPE8 and BPD8

Monoclonal antibodies BPE3, BPE8 and BPD8 specifically detected a single 69 kDa band on Western blots containing cell lysates of serotypes 1.3, 1.3.6, 1.2.3.4, and b 1.2.3.4.6 *B. pertussis* cells, although much greater amounts of antibody were required for detection using antibodies from BPE8 and BPD8 than when antibodies from BPE3 were employed. The 69 kDa band was present in all strains containing serotype 3 agglutinogen, including those not agglutinated by BPE3 monoclonal antibody. No reactivity was observed on immunoblots containing cell lysates of serotype 1 or avirulent strains of *B. pertussis* or other gram-negative organisms.

U.S. Reference Factor 3 antiserum (Eldering agglutinogen 3 polyclonal antiserum) detected a 69 kDa band on identical immunoblots containing *B. pertussis* cell lysates in a pattern consistent with that of monoclonal antibodies BPE3, BPE8 and BPD8.

3. BPD5, BPE6, BPF2, BPB7, BPC10, BPD4, BPD6, BPD9, and BPF5

None of the monoclonal antibodies listed above reacted with boiled fimbriae, however, nonboiled (e.g. boiled for ≦1 minute) type 2 fimbriae were detected with BPF2, BPD5 and BPE6, while type 6 fimbriae were detected with BPC10, BPB7, BPD4, BPD6, BPD9 and BPF5. Those antibodies reactive with type 2 fimbriae did not react with type 6 fimbriae and those antibodies reactive with type 6 fimbriae did not react with type 2 fimbriae.

Previous studies have identified *B. pertussis* fimbriae as serotype 2 and serotype 6 agglutinogens as defined by U.S. Reference Factor antisera (Eldering agglutinogen polyclonal antisera). U. S. Reference Factor 2 antiserum specifically recognized the antigen bound by monoclonal antibody BPD5 only when crude extracts from 325 cells (serotype 1.2.3.4) that contain agglutinogen 2 were used in the assay. Likewise, U.S. Reference Factor 6 antiserum specifically detected the antigen bound by BPC10 only when preparations from 114 cells (serotype 1.3.6) containing agglutinogen 6 were employed in the assay.

No evidence of cross-reactivity of the monoclonal antibodies with unrelated fimbrial agglutinogens was observed. However, some cross-reactivity of both antitype 2 and anti-type 6 monoclonals was observed for fimbriae on *B. bronchiseptica*.

F. Characterization of the Monoclonal Antibodies

The monoclonal antibodies of hybridomas G10F8C3 and E8D8B1 appear to recognize an oligosaccharide epitope on an LOS that is unique for strains of *B. pertussis* and certain strains of *B. bronchiseptica* having a LOS AB profile.

The monoclonal antibodies of hybridomas BPE3, BPE8 and BPD8 appear to recongnize a 69 kDa protein found on the surface of all virulent strains of *B. pertussis*. The monoclonal antibodies were able to strongly agglutinate some *B. pertussis* serotype 1.3.6, 1.2.3.4, or 1.2.3.4.6 strains.

The monoclonal antibodies of hybridomas BPD5, BPE6, BPF2, BPB7, BPC10, BPD4, BPD6, PD9, and BPF5 recognize type 2 or type 6 fimbriae of *B. pertussis*. Of these, only BPF2, BPD5 and BPE6 recognize type 2 fimbriae, while type 6 fimbriae are only detected with BPC10, BPB7, BPD4, BPD6, BPD9 and BPF5. Some, but not all, of these antibodies agglutinated or bound to certain strains of *B. bronchiseptica*.

TABLE 1

Agglutination of bacterial strains by monoclonal antibodies reactive with *B. pertussis* LOS A

| Organism and strain[a] | Agglutination serotype[b] | LOS phenotype[c] | Agglutination titer[d] G10F8C3 | E8D8B1 |
|---|---|---|---|---|
| *B. pertussis* | | | | |
| 460 | 1.2.3.4.6. | AB | 256 | 256 |
| Tohama I | 1.2.3.4. | AB | 2.048 | 1.024 |
| Tohama 325 | 1.2.3.4. | AB | 64 | 64 |
| 150 | 1.2.3.4. | AB | 128 | 64 |
| BP 338 | 1.2.3.4. | AB | 512 | 512 |
| 114 | 1.3.6 | AB | 128 | 64 |
| 432 | 1.3.6. | AB | 256 | 128 |
| BP 353 | 1.3. | AB | 512 | 512 |
| BP 354 | 1.3. | AB | 512 | 512 |
| Tohama III | 1. | AB | 1.024 | 1.024 |
| BP 326 | 1. | AB | 512 | 256 |
| 134 | 1.2.3.4.6. | B | —[e] | — |
| 10901 | Nontypeable[f] | B | — | — |
| 11615 | Nontypeable | B | — | — |
| *B. bronchiseptica* | | | | |
| 058 | | AB | — | — |
| 106 | | AB | — | — |
| 207 | | B | — | — |
| 209 | | AB | — | — |
| *B. parapertussis* | | | | |
| 480 | | B | — | — |
| 482 | | B | — | — |
| 497 | | B | — | — |
| *E. coli* | | | — | — |
| *N. meningitidis* | | | — | — |
| *N. gonorrhoeae* | | | — | — |
| *S. typhimurium* | | | — | — |
| *H. influenzae* | | | — | — |

[a]Bordetella strains were grown on Bordet Gengou blood agar medium, and other gram-negative strains were cultured by routine procedures. Cells were harvested, washed, and treated with 0.2% Formalin.
[b]Agglutination was performed as previously described with Eldering agglutinogen polyclonal antiserum
[c]LOS profile was determined by silver staining, and designations were based on the nomenclature of Peppler. The A and B designations for strains of *B. bronchiseptica* and *B. parapertussis* which may have a number of silver-stained bands denote the presence of silver-stained bands corresponding to the A and B forms of *B. pertussia* LOS.
[d]Agglutination assays were performed with monoclonal antibody preparations (640 μg of protein per ml) partially purified as described in the text. A titer is reported as the inverse of the maximum dilution of antibody which agglutinated the bacteria.
[e]—, Not agglutinated by monoclonal antibody.
[f]Not agglutinated by typing antisera.

TABLE 2

Agglutination of serotype-specific *B. pertussis* strains by monoclonal antibodies and polyclonal antiserum

| *B. pertussis* strain | Agglutinogen serotype[b] | Agglutination titer with the following monoclonal antibodys[a] | | | | | Agglutination titer with mouse anti-69-kDa protein antiserum |
|---|---|---|---|---|---|---|---|
| | | BPE3 | BPE8 | BPD8 | BPF2 | BPC10 | |
| 10901 | Nontypable | —[c] | — | — | — | — | — |
| 11615 | Nontypable | — | — | — | — | — | — |
| Tohama III | 1 | — | — | — | — | — | — |
| BP326 | 1 | — | — | — | — | — | — |
| BP353 | 1.3 | 32.768 | 4.096 | 512 | — | — | 512 |
| BP354 | 1.3 | 32.768 | 4.096 | 512 | — | — | 512 |
| 432 | 1.3.6 | 2.048 | — | — | — | 8.192 | 256 |
| 114 | 1.3.6 | — | — | — | — | 4.096 | 64 |
| BP338 | 1.2.3.4 | 2.048 | 1.024 | 128 | 2.560 | — | 128 |
| 150 | 1.2.3.4 | — | — | — | 2.560 | — | 128 |
| 460 | 1.2.3.4.6 | 4.096 | — | — | 4.096 | 2.048 | 128 |
| 165 | 1.2.3.4.6 | — | — | — | 8.192 | 4.096 | 64 |

[a]*B. pertussis* strains were serotyped by agglutination, as described in Materials and Methods, with U.S. Reference Factor 1 to 6 antisera.
[b]Aglugination assays were performed with concentrated hybridama supernatants or mouse sera pretreated with kaolin, as described in Materials and Methods. Titers are reported as the reciprocal of the maximum antibody dilution which agglutinated the bacteria. Monoclonal antibodies were produced by immunizing mice with *B. pertussis* BP353 cells (BPE3, BPE8, and BPD8) or partially purified type 2 (BPF2) or 6 (BPC10) hmbrise, as described in Materials and Methods.
[c]—, Not agglutinated by antibodies or antiserum at a 1:2 dilution.

TABLE 3

Agglutination of *B. pertussis* cells by monoclonal antibody:[b]

| *B. pertussia* strain | Agglutinogen serotype[a] | Agglutination titer with the following monoclonal antibodies | | | | | | | | |
|---|---|---|---|---|---|---|---|---|---|---|
| | | BPD5(G$_{2a}$) | BPE6(G$_{2b}$) | BPF2(G$_1$) | BPB7(G$_{2b}$) | BPC10(G$_1$) | BPD4(G$_{2a}$) | BPD6(G$_{2a}$) | BPD9(G$_{2a}$) | BPF5(G$_{2b}$) |
| 165 | 1.2.3.4.6 | 16.384 | 8.192 | 8.192 | 256 | 4.096 | 4.096 | 2.048 | 256 | 1.024 |
| 460 | 1.2.3.4.6 | 4.096 | 8.192 | 4.096 | 128[c] | 2.048 | 512 | 256 | 64 | 256 |
| Tohama I | 1.2.3.4 | 4.096 | 8.192 | 4.096 | —[d] | — | — | — | — | — |
| BP325 | 1.2.3.4 | 4.096 | 4.096 | 4.096 | — | — | — | — | — | — |
| 114 | 1.3.6 | — | — | — | 512 | 4.096 | 4.096 | 8.192 | 256 | 512 |
| 432 | 1.3.6 | — | — | — | 512 | 8.192 | 8.192 | 8.192 | 1.042 | 1.042 |
| BP353 | 1.3 | — | — | — | — | — | — | — | — | — |
| BP354 | 1.3 | — | — | — | — | — | — | — | — | — |

TABLE 3-continued

| | | Agglutination of B. pertussis cells by monoclonal antibody:[b] | | | | | | | | |
|---|---|---|---|---|---|---|---|---|---|---|
| B. pertussis strain | Agglutinogen serotype[a] | Agglutination titer with the following monoclonal antibodies | | | | | | | | |
| | | BPD5($G_{2a}$) | BPE6($G_{2b}$) | BPF2($G_1$) | BPB7($G_{2b}$) | BPC10($G_1$) | BPD4($G_{2a}$) | BPD6($G_{2a}$) | BPD9($G_{2a}$) | BPF5($G_{2b}$) |
| Tohama III | 1 | — | — | — | — | — | — | — | — | — |
| BP326 | 1 | — | — | — | — | — | — | — | — | — |
| 10901 | Non-typable | — | — | — | — | — | — | — | — | — |
| 11615 | Non-typable | — | — | — | — | — | — | — | — | — |

[a] B. pertussis cells were serotyped by agglutination, as described with U.S. Reference Factor 1 to 6 antisera.
[b] Agglutination assays were performed with concentrated hybridoma supernatants as described and titers are reported as the reciprocal of the maximum antibody dilution which agglutinated the bacteria. Monoclonal antibodies were produced by immunizing mice with type 2 (BPD5, BPE6, and BPF2) or type 6 (BPB7, BPC10, BPD4, BPD6, BPD9, and BPF5) fimbriae, as described
[c] Monoclonal antibody and antibody subclass.
[d] —, Not agglutinated by a 1:2 dilution of the concentrated hybridoma supernatants.

We claim:

1. A hybridoma, resulting from the fusion of an SP2/0 myeloma cell and a murine spleen cell derived from a mouse immunized with an antigen of *Bordetella pertussis*, wherein said hybridoma produces a monoclonal antibody reactive with a *Bordetella pertussis* antigen wherein said antigen is an oligosaccharide epitope of LOS A.

2. A hybridoma, resulting from the fusion of an SP2/0 myeloma cell and a murine spleen cell derived from a mouse immunized with an antigen of *Bordetella pertussis* serotype 1.3, wherein said hybridoma produces a monoclonal antibody reactive with a *Bordetella pertussis* antigen wherein said antigen is 69 kDa protein.

3. A hybridoma, resulting from the fusion of an SP2/0 myeloma cell and a murine spleen cell derived from a mouse immunized with an antigen of *Bordetella pertussis* serotype 1.2, wherein said hybridoma produces a monoclonal antibody reactive with a *Bordetella pertussis* antigen wherein said antigen is type 2 fimbriae.

4. A hybridoma, resulting from the fusion of an SP2/0 myeloma cell and a murine spleen cell derived from a mouse immunized with an antigen of *Bordetella pertussis* serotype 1.6, wherein said hybridoma produces a monoclonal antibody reactive with a *Bordetella pertussis* antigen wherein said antigen is type 6 fimbriae.

5. Hybridomas designated BPG10F8C3 and BPE8D8B1, said hybridomas producing monoclonal antibodies reactive with an oligosaccharide epitope of LOS A of *B. pertussis*.

6. Hybridomas designated BPE3, BPE8 and BPD8, said hybridomas producing monoclonal antibodies reactive with the 69 kDa protein of *B. pertussis* serotype 1.3.

7. Hybridomas designated BPF2, BPD5 and BPE6, said hybridomas producing monoclonal antibodies reactive with type 2 fimbriae of *B. pertussis* serotype 1.2.

8. Hybridomas designated BPC10, BPB7, BPD4, BPD6, BPD9 and BPF5, said hybridomas producing monoclonal antibodies reactive with type 6 fimbriae of *B. pertussis* serotype 1.6.

9. A monoclonal antibody derived from a hybridoma according to any one of claims 1, 2, 3 or 4.

10. A monoclonal antibody derived from a hybridoma according to claim 5.

11. A monoclonal antibody according to claim 10 wherein said antibody is of the $IgG_3$ class.

12. A monoclonal antibody derived from a hybridoma according to claim 6.

13. A monoclonal antibody according to claim 12 wherein said antibody is of the IgM or $IgG_1$ class.

14. A monoclonal antibody derived from a hybridoma according to claim 8.

15. A monoclonal antibody according to claim 14 wherein said antibody is of the $IgG_1$, $IgG_{2a}$ or $IgG_{2b}$ class.

16. A monoclonal antibody derived from a hybridoma according to claim 8.

17. A monoclonal antibody according to claim 16 wherein said antibody is of the $IgG_1$, or $IgG_{2b}$ class.

18. A diagnostic kit for determining the presence of *Bordetella pertussis* cells or products in clinical materials or laboratory samples, said kit comprising at least one monoclonal antibody according to any one of claims 1, 2, 3 or 4.

* * * * *